United States Patent [19]

Sueptitz

[11] Patent Number: Plant 6,879

[45] Date of Patent: Jun. 27, 1989

[54] CHRYSANTHEMUM PLANT NAMED GOLDEN MAXIMO

[75] Inventor: Dieter Sueptitz, Hamburg, Fed. Rep. of Germany

[73] Assignee: Ball Seed Company, Chicago, Ill.

[21] Appl. No.: 170,453

[22] Filed: Mar. 18, 1988

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Golden Maximo having anemone flower form, golden yellow ray and disc floret color, tubular ray florets which open at the outer ends thereof and taper to a flat apex, vigorous growth habit, 9 week flower response, and an ability to perform well under low light, cool temperature conditions.

1 Drawing Sheet

The present invention comprises a new and distinct cultivar of *Dendranthema grandiflora,* hereinafter referred to by the cultivar name Golden Maximo.

Golden Maximo was discovered as a natural mutation growing in a cultivated, flowering bed of Maximo by Dieter Sueptitz in Hamburg, Germany, in October, 1978. The mutation was immediately recognized by its yellow ray floret color, as opposed to the white ray florets of the parent cultivar. Maximo is disclosed in a pending plant patent application of applicant.

The first act of asexual reproduction of Golden Maximo was accomplished when vegetative cuttings were taken from the initial selection in January 1979 in a controlled environment in Hamburg, Federal Republic of Germany by a technician working under formulations established and supervised by Dieter Sueptitz. Horticultural examination of selected units initiated in April, 1979 has demonstrated that the combination of characteristics as herein disclosed for Golden Maximo are firmly fixed and are retained through successive generations of asexual reproduction.

Golden Maximo has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Golden Maximo, which in combination distinguish this Chrysanthemum as a new and distinct cultivar:

1. Anemone type flower form.
2. Golden yellow ray and disc floret color; immature, unopened disc florets are yellow-green.
3. From the base to about half the ray floret length, the margins are fused forming a tube, with the outer half opening up and the apex of the floret being flat.
4. Disc florets are funnel shaped and up to 12 mm long.
5. Nine week flower response.
6. Very vigorous growth habit, making it suitable for use as a cut flower.
7. Dark green, sharply toothed foliage which is medium to small in size when compared to other cut type Chrysanthemum varieties.

8. Performs well under low light, cool temperature conditions.

Of the many cultivars known to the present inventor, the most similar in comparison to Golden Maximo is its parent Maximo. Except for ray floret color, Golden Maximo is similar in all essential respects to Maximo. Comparison can also be made to the well known commercial cultivar Hoof Lane. Reference is made to Chart A which compares certain characteristics of Golden Maximo to those same characteristics of Hoof Lane. In comparison to Hoof Lane, Golden Maximo has slightly darker yellow ray florets, a more vigorous growth habit, more sharply toothed foliage, a larger disc, and the disc of Golden Maximo does not display a "dark eye" when grown under cool temperatures as Hoof Lane does. The flower type and diameter, and the number of ray florets of Golden Maximo are similar to those same characteristics of Hoof Lane.

The accompanying photographic drawing shows typical inflorescence and foliage characteristics of Golden Maximo, with colors being as nearly true as possible with illustrations of this type. The photograph is in black and white, with one flower being colored to accurately depict true ray and disc floret color.

In the following description, color references are made to The Royal Horticultural Society Colour Chart. The color values were determined between 8:00 and 8:30 a.m. on Dec. 31, 1987 under fluorescent lighting at Parrish, Fla.

Classification:

*Botanical.*—*Dendranthema grandiflora,* cv. Golden Maximo.

*Commercial.*—Cut anemone spray.

INFLORESCENCE

A. Capitulum:

*Form.*—Flat.

*Type.*—Anemone.

*Diameter across face.*—6-7.7 cm.

B. Corolla of ray florets:

*Color (general tonality from a distance of three meters).*—Yellow.

*Color (upper surface).*—6A.

*Color (under surface).*—6D.

C. Corolla of disc florets:

*Color* (*mature*).—13B just prior to opening, then fading to 7A as flower ages.

*Color* (*immature*).—Yellow-green 149B.

D. Reproductive organs.

*Androecium.*—Present in disc florets only.

*Gynoecium.*—Present in both disc and ray florets.

PLANT

A. General appearance:

*Height.*—95 cm when grown unpinched and given 2 weeks of long days before short days begin.

B. Foliage:

*Color* (*upper surface*).—147A.

*Color* (*under surface*).—147B.

*Shape.*—Ovate, deeply lobed and serrated.

CHART A

| | Golden Maximo | Hoof Lane |
|---|---|---|
| Flower diameter | 6 cm–7.7 cm | 6–7 cm |

CHART A-continued

| | Golden Maximo | Hoof Lane |
|---|---|---|
| Average number of ray florets | 32.5 | 32 |
| Height of flowering plant given 2 weeks of long days | 95 cm | 70 cm |
| Fully expanded ray floret width | 7–9 mm | 7–10 mm |
| Fully expanded ray floret length | 32–37 mm | 25–30 mm |
| Flower response after onset of short days | 9 weeks | 8.5 weeks |
| Ray floret color | 6 A | 3 B |
| Diameter of disc | 35–43 mm | 22–27 mm |
| Mature disc floret color | 7 A | 9 A |
| Disc floret length | 12–19 mm | 9–12 mm |

I claim:

1. A new and distinct cultivar of Chrysanthemum plant named Golden Maximo, as illustrated and described, and parts thereof.

* * * * *

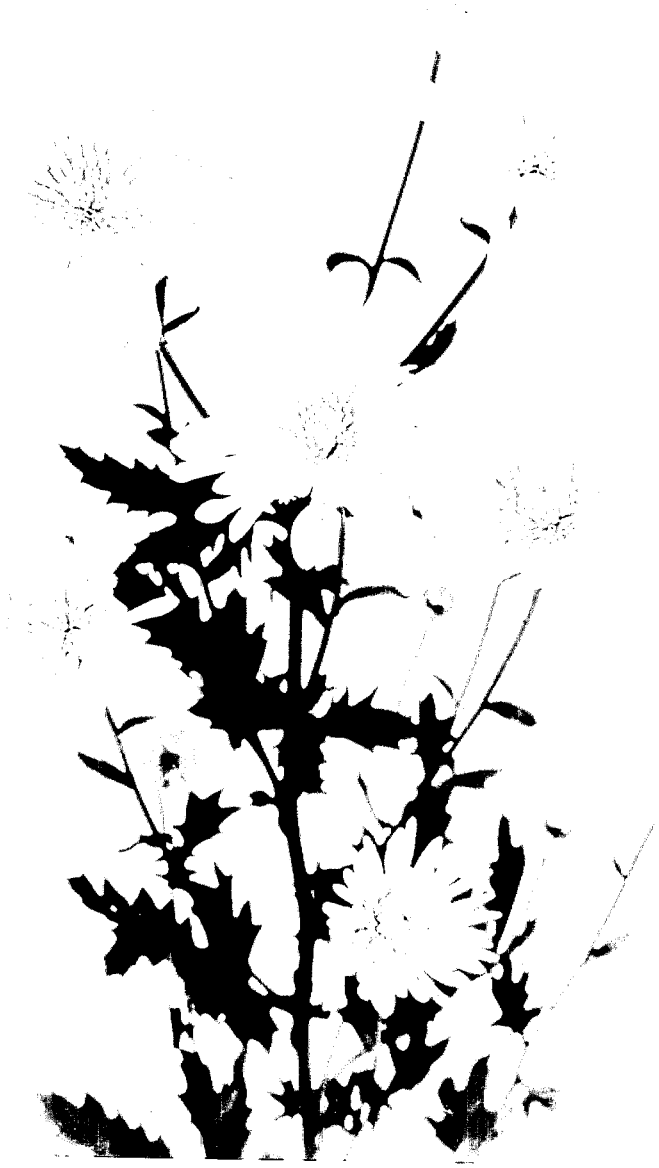

U.S. Patent Jun. 27, 1989 Plant 6,879